(12) United States Patent
Hey et al.

(10) Patent No.: US 10,039,615 B2
(45) Date of Patent: Aug. 7, 2018

(54) METHOD FOR PLANNING A ROOT TREATMENT OF A PATIENT

(71) Applicant: SICAT GMBH & CO. KG, Bonn (DE)

(72) Inventors: Joachim Hey, Koenigswinter (DE); Jochen Kusch, Wachtenberg-Pesch (DE); Andreas Zollorsch, Bonn (DE)

(73) Assignee: SICAT GMBH & CO. KG, Bonn (DE)

( * ) Notice: Subject to any disclaimer, the term of this patent is extended or adjusted under 35 U.S.C. 154(b) by 67 days.

(21) Appl. No.: 14/779,974

(22) PCT Filed: Mar. 21, 2014

(86) PCT No.: PCT/EP2014/055712
§ 371 (c)(1),
(2) Date: Sep. 25, 2015

(87) PCT Pub. No.: WO2014/154584
PCT Pub. Date: Oct. 2, 2014

(65) Prior Publication Data
US 2016/0030136 A1  Feb. 4, 2016

(30) Foreign Application Priority Data
Mar. 28, 2013  (DE) .................. 10 2013 103 209

(51) Int. Cl.
*A61C 1/08* (2006.01)
*A61B 5/00* (2006.01)
(Continued)

(52) U.S. Cl.
CPC ............ *A61C 5/025* (2013.01); *A61B 5/0088* (2013.01); *A61C 1/082* (2013.01);
(Continued)

(58) Field of Classification Search
CPC .. A61C 5/025; A61C 5/42; A61C 5/44; A61C 1/082; A61C 2034/105; A61B 5/0088
See application file for complete search history.

(56) References Cited

U.S. PATENT DOCUMENTS 3,772,791 A * 11/1973 Malmin .................. A61C 5/44
                                                           433/224
4,144,645 A *  3/1979 Marshall ................. A61C 5/77
                                                           433/223
(Continued)

FOREIGN PATENT DOCUMENTS

CA    2 835 756 A1    11/2012
DE    37 34 303 A1     4/1989
(Continued)

*Primary Examiner* — Cris L Rodriguez
*Assistant Examiner* — Hao D Mai
(74) *Attorney, Agent, or Firm* — Norman B. Thot

(57) ABSTRACT

A method for planning a root canal treatment of a tooth which includes a cavity of a patient. The method includes measuring a surface of the cavity with an optical three-dimensional method to generate three-dimensional measurement data of the cavity. A 3D-model of a guide template is planned based on the generated three-dimensional measurement data. The 3-D model is designed in its dimensions as a counterpart to the cavity. Three-dimensional volume data of the tooth is displayed. A position and an orientation of a root canal of the tooth is determined based on the three-dimensional volume data of the tooth. A guide opening for a tool is planned to expose the root canal. The guide opening is arranged within the guide template so that the guide opening points at an entry point of the root canal and in an entry direction of the root canal.

9 Claims, 3 Drawing Sheets

(51) Int. Cl.
*A61B 34/10* (2016.01)
*A61C 5/42* (2017.01)
*A61C 5/44* (2017.01)
*A61C 5/02* (2006.01)

(52) U.S. Cl.
CPC ........... *A61B 2034/105* (2016.02); *A61C 5/42* (2017.02); *A61C 5/44* (2017.02)

(56) References Cited

U.S. PATENT DOCUMENTS

| | | | | |
|---|---|---|---|---|
| 5,658,149 | A * | 8/1997 | Munce | A61C 5/40 433/102 |
| 6,319,006 | B1 * | 11/2001 | Scherer | A61C 1/084 433/215 |
| 6,358,049 | B1 * | 3/2002 | Cerniway | A61C 5/44 33/513 |
| 7,346,417 | B2 * | 3/2008 | Luth | A61B 34/20 128/920 |
| 8,177,554 | B2 * | 5/2012 | Krasner | A61C 5/40 433/72 |
| 8,805,658 | B2 * | 8/2014 | Pettersson | A61B 17/8685 703/6 |
| 9,402,693 | B2 * | 8/2016 | Colby | A61C 1/082 |
| 2002/0119432 | A1 * | 8/2002 | Ranta | G09B 23/283 434/263 |
| 2004/0219482 | A1 * | 11/2004 | Bina | A61C 5/44 433/75 |
| 2007/0154862 | A1 | 7/2007 | Kim | |
| 2010/0203479 | A1 * | 8/2010 | Bulloch | A61C 8/0089 433/215 |
| 2012/0143364 | A1 * | 6/2012 | Mcleod | A61C 1/082 700/98 |
| 2013/0144417 | A1 | 6/2013 | Pieper | |
| 2013/0171580 | A1 | 7/2013 | Van Lierde et al. | |
| 2014/0322664 | A1 * | 10/2014 | Van Lierde | G06F 19/3437 433/72 |
| 2016/0143717 | A1 * | 5/2016 | Samrano | A61C 1/082 29/896.1 |
| 2017/0065370 | A1 * | 3/2017 | Nakai | A61B 6/03 |

FOREIGN PATENT DOCUMENTS

| | | |
|---|---|---|
| DE | 199 52 962 A1 | 5/2001 |
| DE | 10 2010 031 018 A1 | 1/2012 |
| JP | 2007-512079 A | 5/2007 |
| WO | WO 2011/101447 A2 | 8/2011 |

* cited by examiner

METHOD FOR PLANNING A ROOT TREATMENT OF A PATIENT

CROSS REFERENCE TO PRIOR APPLICATIONS

This application is a U.S. National Phase application under 35 U.S.C. § 371 of International Application No. PCT/EP2014/055712, filed on Mar. 21, 2014 and which claims benefit to German Patent Application No. 10 2013 103 209.5, filed on Mar. 28, 2013. The International Application was published in German on Oct. 2, 2014 as WO 2014/154584 Al under PCT Article 21(2).

FIELD

The present invention relates to a method for planning a root canal treatment of a patient using three-dimensional volume data of the tooth to be treated. A drilling aid may thereby be used.

BACKGROUND

A typical method for root canal treatment is to remove inflamed dental pulp to save the tooth, even if the tooth is then dead. For removing the dental pulp, the root canal must be precisely exposed and sanitized so that it can subsequently be sealed. The entrance into the affected root canal must therefore first be found. The canal is subsequently exposed with a file, wherein the intent is to expose the canal exactly up to the root tip.

Locating the entrance to a root canal is based widely on the experience of the dentist. It is extremely difficult to find the entrances in the area of the molar tooth since multiple root canals are here present, which may also be strongly curved in its course. The number of root canals and their course cannot always be clearly determined based on panoramic radiographs or single tooth scans.

If an incorrect path is found which misses the actual root canal, the inflamed root is not removed and the subsequent root canal treatment is a priori deemed to fail.

For implant planning, DE 199 52 962 A1 describes creating a drilling aid using surface data and 3D data.

SUMMARY

An aspect of the present invention is to improve the possibilities of dental practitioners in preparing the treatments of a root canal.

In an embodiment, the present invention provides a method for planning a root canal treatment of a tooth of a patient, wherein the tooth comprises a cavity. The method includes measuring a surface of the cavity with an optical three-dimensional method so as to generate three-dimensional measurement data of the cavity. A 3D-model of a guide template is planned based on the generated three-dimensional measurement data. The 3-D model is designed in its dimensions as a counterpart to the cavity. Three-dimensional volume data of the tooth is displayed. A position and an orientation of at least one root canal of the tooth is determined based on the three-dimensional volume data of the tooth. At least one guide opening for a tool which is configured to expose the at least one root canal is planned. The at least one guide opening is arranged within the guide template so that the at least one guide opening points at an entry point of the at least one root canal and in an entry direction of the at least one root canal.

BRIEF DESCRIPTION OF THE DRAWINGS

The present invention is described in greater detail below on the basis of embodiments and of the drawings in which.

DETAILED DESCRIPTION

Figure 1:
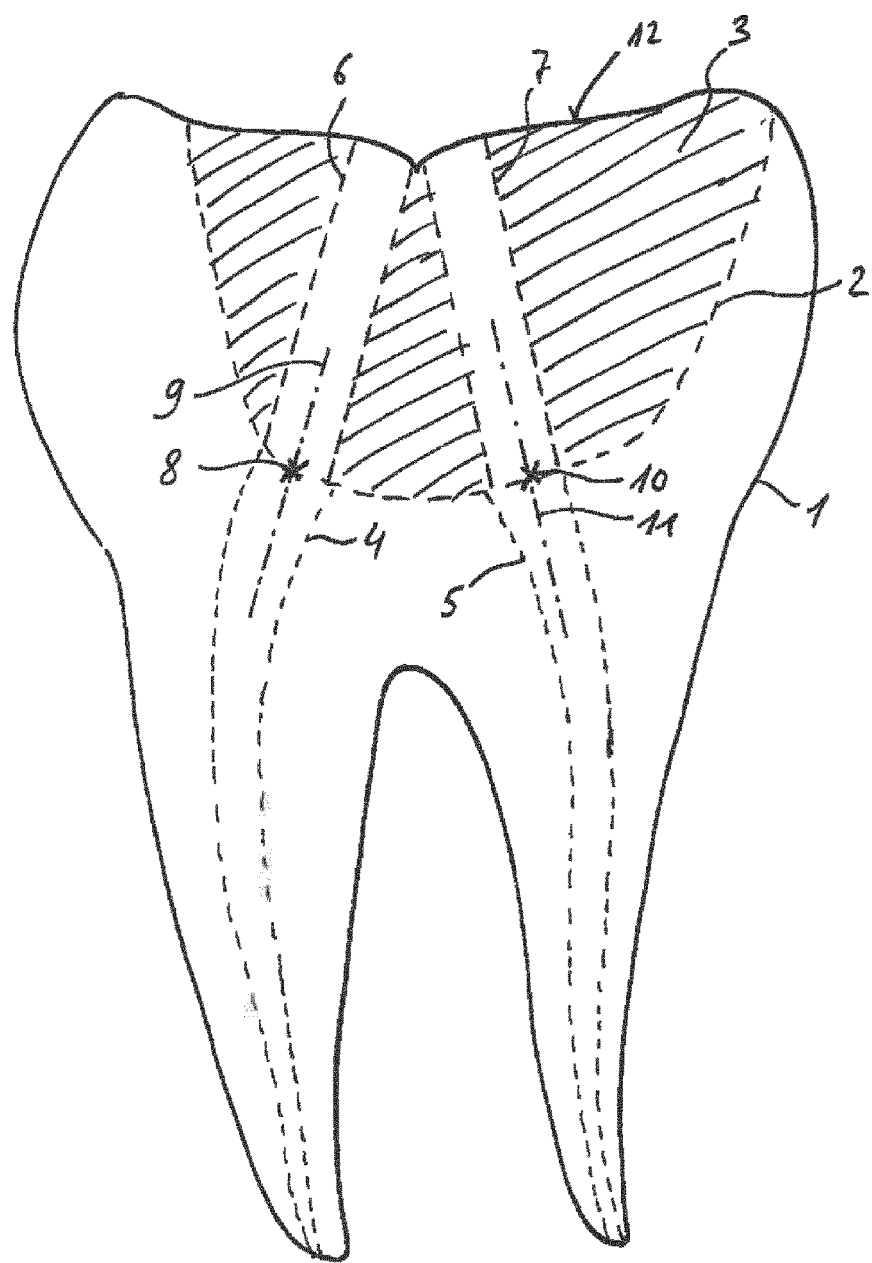
FIG. 1 shows a method for planning a root canal treatment.

The present invention relates a method for planning a root canal treatment of a patient, wherein a cavity in a tooth to be treated is already prepared, wherein a surface of the cavity is measured by an optical three-dimensional measuring method to thereby generate three-dimensional measuring data of the cavity. Based on the generated three-dimensional measurement data, a 3D model of a guide template is planned, which is designed in its dimensions as a counterpart to the prepared cavity. Based on three-dimensional volume data of the tooth to be treated, a position and an orientation of at least one root canal is determined, wherein at least one guide opening for a tool to expose the root canal is planned. The guide opening is arranged within the guide template so that the guide opening points to an entry point of the root canal and in a direction of entry of the root canal.

After determining the location and orientation of the root canals relative to the tooth to be treated, the direction of entry and the entry point of the root canals are also defined. The treatment can thereby be carried out more quickly and more efficiently without requiring the unnecessarily removal of the dentine and the tooth crown.

The entry point may, for example, lie at an end of the root canal facing the oral cavity.

The necessary three-dimensional volume data of the tooth and its internal structure can, for example, be obtained with the help of a dental X-ray machine on the basis of cone-beam technology. This 3D data is used, with the aid of a computer program, to identify the root canals and to define the exact direction of entry and the length of the individual root canal, for example, with respect to a predetermined plane. The root canals can then be marked in the program so that a root canal planning is possible.

The location of the entry point and the orientation of the direction of entry of each of the root canals is determined in relation to the surrounding anatomical structures, such as the adjacent teeth. This referencing and/or registration can be performed using certain distinctive anatomical structures of the 3D-data, such as structures on the occlusal surfaces of the adjacent teeth, or using special markers which can be arranged on an attachment part or on a bite splint. During the recording to generate the set of 3D data, this attachment part can be attached in the oral cavity of the patient at the tooth to be treated and/or on the adjacent teeth. The 3D record is obtained by this unique positional relationship between the position and orientation of the individual root canals and the surrounding anatomical structures.

The optical three-dimensional measurement method to generate the three-dimensional measurement data cavity can, for example, be a structured-light 3D scanner projection method. The guide template is designed as a counterpart to the prepared cavity so that the guide template can be accurately fitted into the cavity so as to allow a precise machining of the root canal.

The X-ray data to determine the orientation of the root canal relative to the tooth to be treated can be generated even before the measurement of the preparation. The determination of the entry point and the direction of entry of the root canals can be carried out on the basis of X-ray data manually by the user or automatically based on computer-assisted pattern recognition algorithms.

An advantage of this method is that the guide template is designed as a counterpart to the prepared cavity, which has a corresponding guide opening, the guide opening points exactly on the entry point and the direction of entry of the root canal. This enables an error free root canal treatment, wherein the root canal can be treated exactly by the tool to expose the root canal without unnecessarily removing the surrounding tooth substance.

The production of the guide template can, for example, be performed fully automatically by a CAD/CAM system from a blank.

In the root canal treatment, a filling volume for a filler material can advantageously be determined based on the known dimensions of the tool to be used and based on a depth of immersion of the tool into the root canal. This prevents too much injected filler material from emerging at the tip of the root and causing complications there. An overfill of the root canal is thus prevented.

The present method provides that any machining tool or a combination of several machining tools can be selected in order to expose the root canal as gently to tissue as possible. The machining tool can thereby be designed, for example, to be cylindrical or tapered to a tip.

The volume can therefore be calculated before the machining of the tooth under consideration of the dimensions of the selected machining tool.

If the root canal is exposed with a single machining tool, the drill hole has a cylindrical shape. Its volume can thus be calculated from its length and diameter.

If the root canal is exposed using a plurality of machining tools with decreasing diameter, the drill hole will have a step-like shape which narrows in a direction to the root canal tip. The volume of the drilling canal can then also be determined from the sum of the individual distances of the same diameter. If the root canal is exposed using a conical machining tool, the volume can be calculated using the dimension of the machining tool and the depth of immersion relative to the entry point.

Several tools with increasing diameter and decreasing depth of immersion can advantageously be used to expose the root canal so that the filling volume is calculated based on the known dimensions of the individual tools and the planned depth of immersion for each of the tools.

A machining tool which is appropriate in thickness can therefore be selected, usually a drill or a file. The thickness of the root canal can be reduced to the root tip. One possibility of treatment is that the root canal is exposed throughout its complete length with a broad processing tool having a diameter of the starting point of the root canal at the entry point.

A further possible treatment of the root canal involves selecting more machining tools of a decreasing diameter which are used subsequently to completely expose the narrowing root canal, step by step, without removing the tooth material surrounding the root canal.

A single machining tool can alternatively be used which is tapered toward the tip and whose dimensions correspond to the dimensions of an average root canal.

The advantage of such a change is that the root canal can be exposed particularly gently with respect to the surrounding tooth tissue.

The length and the position of the root canal is therefore already determined in the planning stage via this method so that a suitable machining tool or a plurality of machining tools with increasing diameter can subsequently be selected to very gently expose the root canal. The depth of immersion relative to the entry point can thereby be planned before treatment for each of the selected machining tools.

The planned guide template can advantageously be produced by a processing machine.

The production of the guide template can, for example, occur fully automatically and computer-assisted by a CAD/CAM system, wherein the guide template is fully automatically grinded from a blank based on the planned 3D model.

An end face of the guide template can advantageously be designed as a flat surface which is arranged perpendicular to a tooth axis.

The flat end face can thereby be used as a stop for the machining tool.

An end face of the guide template can advantageously correspond to an occlusal surface of the tooth to be treated.

The end face can correspond to the occlusal surface of the original tooth or also be newly planned based on the measurement data of the adjacent teeth and the opposing teeth. Such a guide template can be used as an inlay after the root canal treatment, whereby only the guide canal is reclosed.

An inlay can advantageously be produced from the guide template by closing the guide opening or the guide template can be used as a template to produce an inlay.

The production of an inlay after the root canal treatment is thus facilitated. The guide opening may be closed by a suitable material such as dental cement.

The production of the guide template can advantageously occur fully automatically by a CAD/CAM system from a blank according to a processing plan.

In a first step, the 3D-model of the guide template, which was planned by a CAD unit, is translated into the working plan which comprises several machine instructions. These machine instructions are, in a second step, then transmitted to a CAM unit, such as a conventional processing machine with a plurality of milling tools. Subsequently, in a third step, the planned drilling template is fully automatically processed out of the blank clamped in the machine tool.

The manufacturing process of the guide template is thus simplified and accelerated.

Another aspect of the present invention is to provide a guide template for a root canal treatment of a patient, the guide template comprising at least one guide opening. The guide template has a lateral surface which is formed as a counterpart to a prepared cavity of a tooth to be treated, wherein the guide opening points to an entry point in a direction of entry of at least one root canal of the tooth to be treated.

This guide template has the advantage that it is shaped as a counterpart to the prepared cavity and thus enables a unique positioning relative to the tooth to be treated. Positioning errors at the root treatment can thus be prevented.

Another advantage of this guide template is that the root canal can be performed with a view to maximize tissue preservation, whereby the tooth material surrounding the entry point of the root canal does not need to be removed.

An end face of the guide template can advantageously be designed as a flat surface which is arranged perpendicular to a tooth axis of the tooth to be treated.

The flat end face can thereby be used as a positioning aid for the user and as a stop surface for the tool.

An end surface of the guide template can advantageously be designed as an occlusal surface of the tooth to be treated.

An inlay can therefore be manufactured from the guide template in a simple manner which matches the occlusal surface, whereby only the guide opening is closed with a suitable material, such as with dental cement.

FIG. 1 illustrates the method for planning a root canal treatment. At a tooth 1 to be treated, a cavity 2 is already prepared. In a first method step, this cavity 2 is measured by an optical three-dimensional measurement method while three-dimensional measurement data of the cavity 2 is generated. Based on the generated measurement data, in the second process step, a 3D model of a guide template 3, which is illustrated by dashed lines, is planned, wherein the guide template 3 is formed in its dimensions as a counterpart to the cavity 2. Based on X-ray data of the tooth 1 to be treated, the position and orientation of a first root canal 4 and a second root canal 5 is determined. Subsequently, a first guide opening 6 and a second guide opening 7 is planned within the guide template 3 so that the first guide opening 6 points to a first entry point 8 of the first root canal 4 in a first direction of entry 9, and so that the second guide opening 7 points to a second direction of entry 10 of the second root canal 5 shows in a second direction of entry 11. After planning the 3D model, the guide template 3 is produced by means of a CAM-processing machine and, as shown in FIG. 1, precisely inserted into the prepared cavity 2. The root treatment is then performed by a tool suitable to expose the root canal, wherein the tool is guided by the root canals 4 and 5 as guide holes. After performing the root treatment, the guide template 3 can also be used for the production of an inlay, wherein the root canals 4, 5 are filled with a suitable material, such as dental cement. Such an inlay can then be inserted precisely into the preparation. The guide template shown in FIG. 1 has an end face 12 which is shaped as a occlusal surface of the tooth to be treated. The end face 12 may also be shaped as a flat surface.

Figure 2:
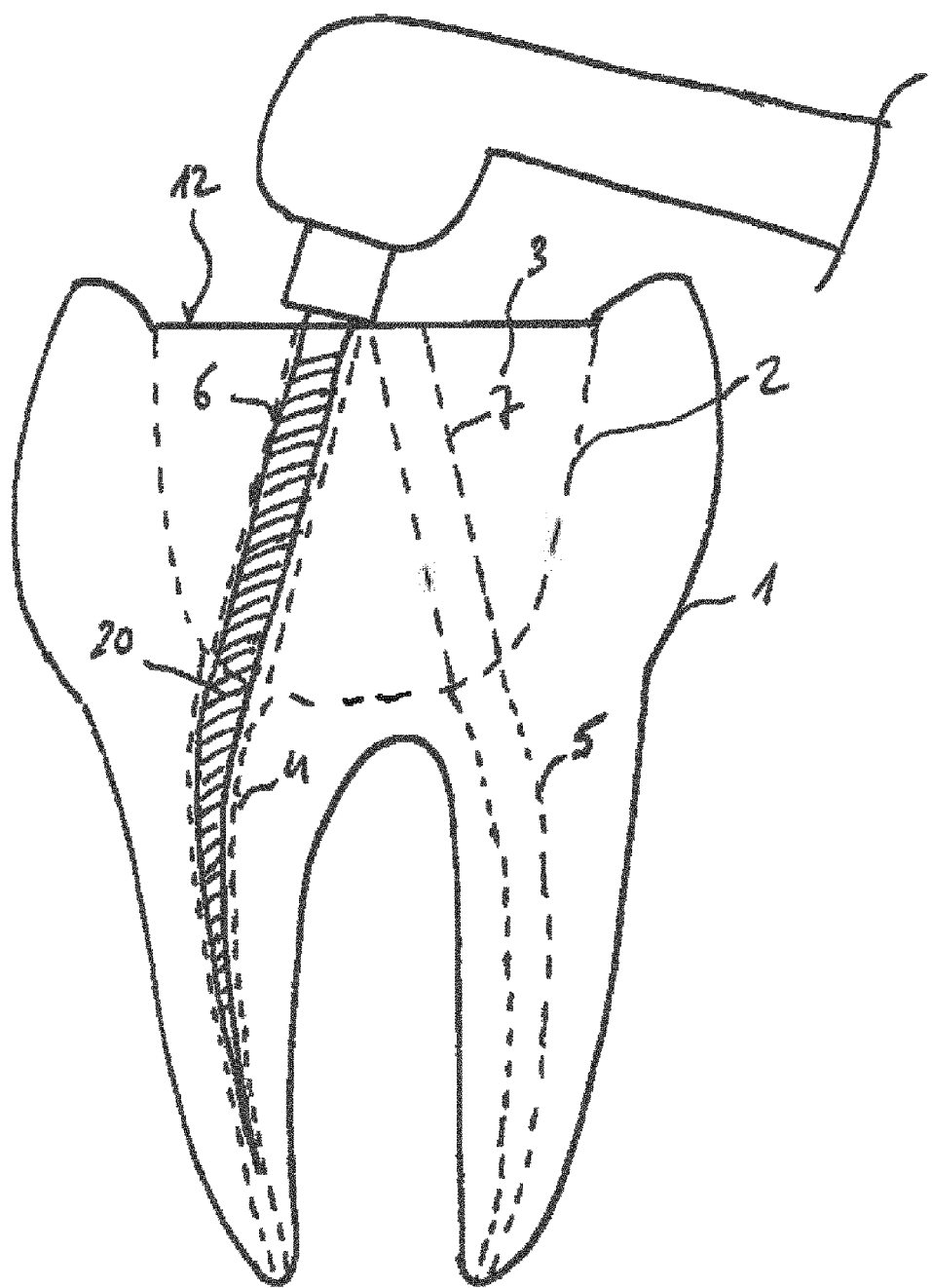
FIG. 2 shows a diagram to illustrate the implementation of the root canal using a special tool.

FIG. 2 illustrates the implementation of the root treatment by the guide template 3. To expose the root canals 4, 5, a special tool 20 is used, which is in the present case designed as a tapered flexible file. The tool 20 is therefore guided by the respective guide opening 6, 7 so that it can immerse positionally accurately into the respective root canal 4, 5. The end face 12, which is in the present case designed as a planar surface, serves as a stop for the tool 20, which defines the depth of immersion of the tool 20 into the respective root canal 4, 5. A filling volume of the filling material can be determined based on the dimensions of the tool 20 to be used and based on the depth of immersion of the tool into the respective root canal 4, 5. This filling material is injected into it to the respective root canal 4, 5 up to the respective entry point 8, 10, after the respective root canals 4, 5 are exposed. The determination of the filling volume is important because an insufficient filling volume may lead to an insufficient root treatment in the upper segment of the root canal and a filling volume which is too high may lead to an overfill of the respective root canal 4, 5. An exit of the filling material from to the tip ends of the respective root canals 4, 5 of the tooth 1 may lead to damage of nerves, which are arranged at this point. To expose the root canal 4, 5, several tools with increasing diameter and decreasing depth of immersion can also be used; the tools may be shaped conically or also cylindrically.

Figure 3:
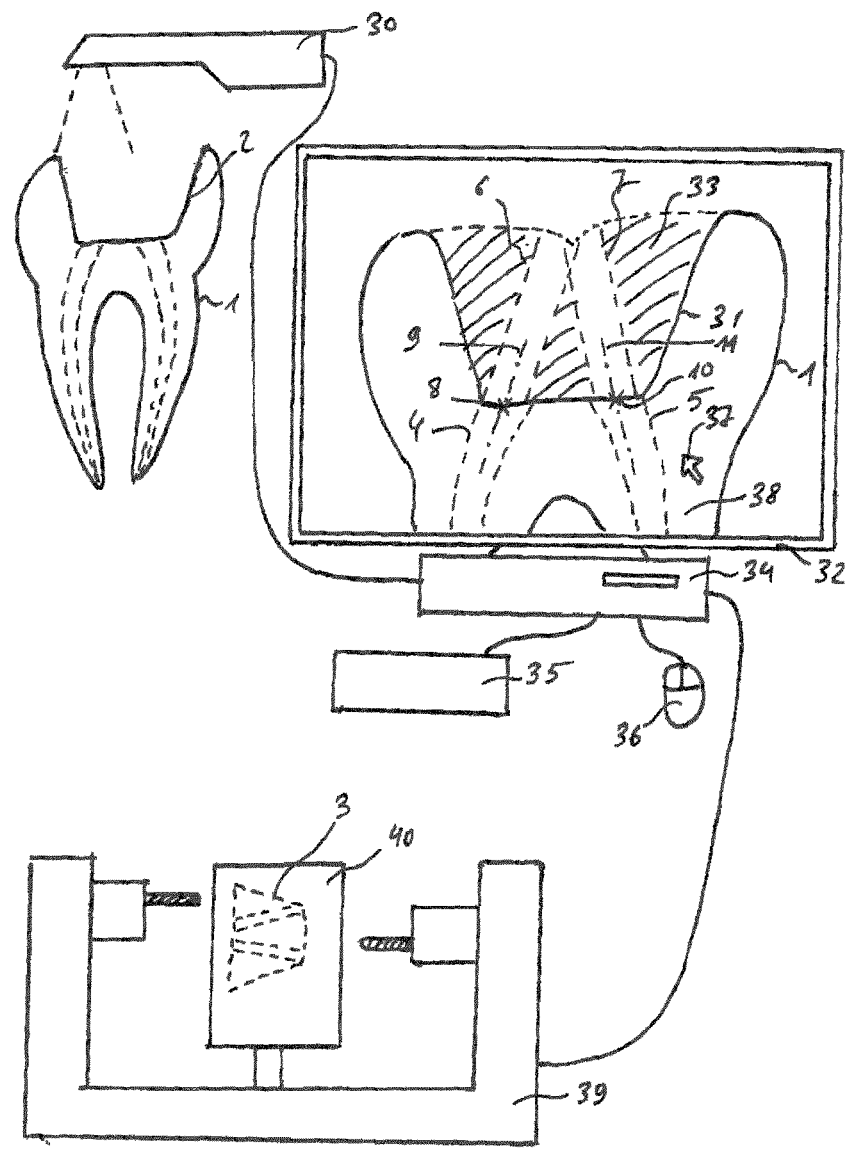
FIG. 3 shows the design by a computer.

FIG. 3 illustrates the method for planning the root treatment. In a first method step, the cavity 2 of the tooth 1 to be treated is measured by a camera 30, which is based on a structured-light 3D scanner projection technology. The generated three-dimensional measurement data 31 of the cavity 2 are displayed by a display device, such as a monitor 32. A 3D model 33 of guide template 3 is subsequently planned based on the generated three-dimensional measured data 31, which is shaped in its dimensions as a counterpart of the cavity 2. During planning, the guide openings 6 and 7 are planned in the 3D model so that they point to the entry points 8, 10 in the direction of entry 9, 11 of the root canals 4, 5. The planning is done virtually by a computer 34, to which the input devices, such as the keyboard 35 and mouse 36, are connected. A cursor 37 may be used to select and position the guide opening 6, 7 within the 3D model 33. In superposition with the (optical) three-dimensional measured data 31, X-Ray data 38 of the tooth to be treated are displayed which allow a determination of the position and orientation of the root canals 4, 5. The planned guide template 3 is then grinded out of a blank 40 fully automatically by a CAM machine 39 following the 3D model 33. The produced guide template 3 can then (as shown in FIG. 1) be inserted in the cavity 2 to carry out the planned root treatment.

The present invention is not limited to embodiments described herein; reference should be had to the appended claims.

LIST OF REFERENCE NUMBERS 1 tooth
2 cavity/preparation
3 guide template
4 first root canal
5 second root canal
6 first guide opening
7 second guide opening
8 first entry point
9 first direction of entry
10 second entry point
11 second direction of entry
12 end face
20 tool
30 camera
31 three-dimensional measurement data
32 monitor
33 3D model
34 computer
35 keyboard
36 mouse
37 cursor
38 X-ray data
39 CAM machine
40 blank

What is claimed is:

1. A method for producing a guide template for a root canal treatment of a tooth of a patient, wherein the tooth comprises a prepared cavity comprising an opening in an occlusal area of the tooth, the method comprising:

measuring a surface of the prepared cavity with an optical three-dimensional method so as to generate three-dimensional measurement data of the prepared cavity including inner dimensions of the prepared cavity, the optical three-dimensional method comprising an optical scanning instrument;

providing three-dimensional volume data of the tooth via an X-ray machine using cone-beam technology;

planning a 3D-model of a guide template based on the generated three-dimensional measurement data, the 3D-model having exterior dimensions corresponding to the inner dimensions of the prepared cavity;

determining a position and an orientation of at least one root canal of the tooth based on the three-dimensional volume data of the tooth being merged in superposition with the three-dimensional measurement data of the prepared cavity;

wherein the step of planning the 3D model of the guide template further comprises planning at least one guide opening within the 3D-model of the guide template based on the determined position and orientation of the at least one root canal such that the at least one guide opening points at an entry point and in an entry direction of the at least one root canal, the at least one guide opening is for guiding a tool which is configured to expose the at least one root canal; and producing a physical guide template based on the planned 3D-model of the guide template via a CAD/CAM system, wherein the physical guide template includes at least one physical guide opening based on the planned at least one guide opening, wherein the planning of the 3D-model of the guide template, the determining of the position and the orientation of the at least one root canal of the tooth, and the planning of the at least one guide opening for the tool are each performed using a computer and with the aid of a computer program haying the three dimensional measurement data of the prepared cavity and the three-dimensional volume data of the tooth inputted therein.

2. A root canal treatment method using the physical guide template as recited in claim 1, the method comprising:

providing the physical guide template; and using the physical guide template to determine a filling volume for a filler material based on a known dimension of the tool and based on a depth of immersion of the tool into the at least one root canal.

3. The root canal treatment method as recited in claim 2, further comprising:

exposing the at least one root canal; and using a plurality of tools having an increasing diameter and a decreasing penetration depth to expose the at least one root canal, wherein, the filling volume is calculated from the respective known dimension of each of the plurality of tools and the planned depth of immersion of each of the plurality of tools.

4. The method as recited in claim 1, wherein the physical guide template comprises an end face which is arranged perpendicular to an axis of the tooth.

5. The method as recited in claim 4, wherein the end face of the physical guide template conforms to an occlusal surface of the tooth.

6. The method as recited in claim 1, further comprising: producing an inlay from the physical guide template by closing the at least one guide opening.

7. The method as recited in claim 1, further comprising: using the physical guide template as a template to produce an inlay.

8. The method as recited in claim 1, wherein the producing of the guide template via the CAD/CAM system is preformed automatically from a blank according to a processing schedule.

9. The method as recited in claim 1, further comprising: providing a processing machine; and
using the processing machine to produce the physical guide template.

* * * * *